United States Patent [19]

Ikuno

[11] 4,284,338
[45] Aug. 18, 1981

[54] PHOTOGRAPHING APPARATUS FOR AN ENDOSCOPE

[75] Inventor: Yuji Ikuno, Hino, Japan

[73] Assignee: Olympus Optical Co., Ltd., Tokyo, Japan

[21] Appl. No.: 119,008

[22] Filed: Feb. 6, 1980

[30] Foreign Application Priority Data

Feb. 14, 1979 [JP] Japan .................................. 54/15628

[51] Int. Cl.³ .................... G03B 7/083; A61B 1/04
[52] U.S. Cl. ........................................ 354/32; 354/50; 354/62; 354/173
[58] Field of Search .................. 354/32–35, 354/50, 51, 60 R, 62, 173, 128, 234, 235, 266–269; 128/4–9

[56] References Cited

U.S. PATENT DOCUMENTS 3,599,630   8/1971   Sato et al. ..................... 354/62 X

FOREIGN PATENT DOCUMENTS 2703664   8/1978   Fed. Rep. of Germany ............. 354/62
48-32724  10/1973  Japan .
54-12503   1/1979  Japan .

*Primary Examiner*—L. T. Hix
*Assistant Examiner*—W. J. Brady

[57] ABSTRACT

A camera for an endoscope has a transmitting circuit for transmitting a release signal and a modulated signal modulated by a photocurrent signal, and a superposing circuit for superposing the modulated signal onto a motor drive line connecting to a film wind motor. A light source unit has a demodulated circuit for demodulating the modulated signal transmitting from the transmitting circuit, through the motor drive line. An exposure measuring circuit calculates an optimum exposure by using the demodulated signal from the demodulating circuit.

7 Claims, 8 Drawing Figures

PHOTOGRAPHING APPARATUS FOR AN ENDOSCOPE

The invention relates to a photographing apparatus for making an automatic exposure photograph through the combination of a light source unit, an endoscope and a camera for endoscope photograph.

In the conventional photographing apparatus for an endoscope, a power supply and an exposure measuring circuit are provided in a light source unit, and a photosensor is provided in an endoscope. The power source provided in the light source unit is connected to a film wind motor provided in a camera, through a terminal. The photosensor in the endoscope is connected through a terminal to an exposure measuring circuit within the light source. A release switch of the camera is connected through a terminal to the exposure measuring circuit. As described above, the conventional this type photographing apparatus needs a relatively large number of terminals for the electrical connection among the light source unit, the endoscope and the camera. The electrical connection by terminal often suffers from poor contact and the poor contact more frequently occurs as the number of the terminals becomes larger. Further, with increase of the number of terminals, the connection structure is complicated and cleaning of the terminals is troublesome.

An object of the invention is to provide a photographing apparatus for an endoscope which reduces the number of terminals and improves the accuracy of an automatic exposure photograph.

According to the invention, there is provided a photographing apparatus for an endoscope for making an automatic exposure photograph through the combination of a light source unit, an endoscope and a camera for endoscope photograph, wherein the camera for endoscope photograph includes a photosensing element for producing a photocurrent signal, a transmitting circuit for transmitting a release signal produced in response to the operation of a release switch and a modulated signal modulated by the photocurrent signal derived from the photosensing element, and a superposing circuit for superposing the modulated signal onto a motor drive line connecting to a film wind motor, and the light source unit includes a demodulating circuit for demodulating the demodulated signal transmitted from the transmitting circuit and an exposure measuring circuit for measuring an optimum exposure by using a demodulated signal from the demodulating circuit.

Other objects and features of the invention will be apparent from the following description taken in connection with the accompanying drawings in which.

Embodiments of the invention will be described in detail with reference to accompanying drawings.

Figure 1:
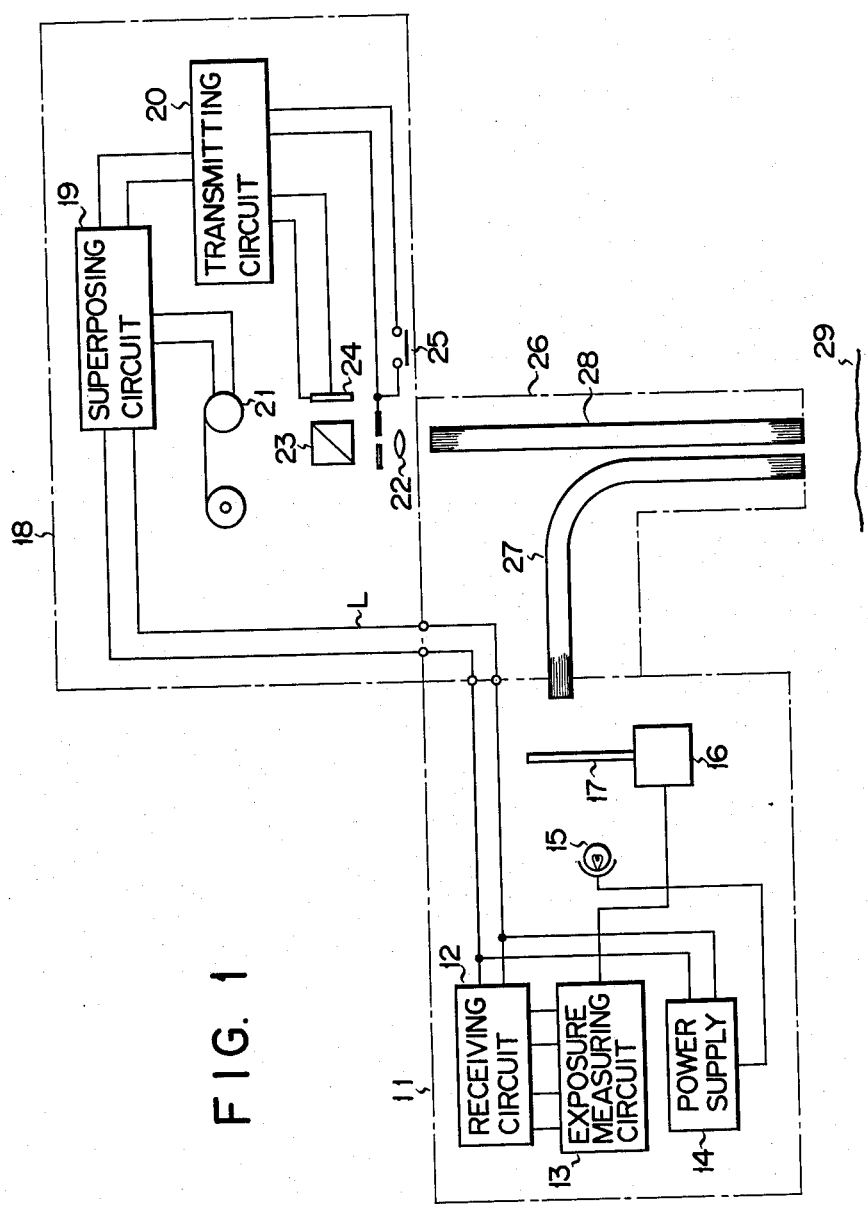
FIG. 1 shows a block diagram of a photographing apparatus for an endoscope which is an embodiment of the invention.

Referring now to FIG. 1, there is shown an embodiment of a photographing apparatus for an endoscope according to the invention. In the figure, a light source unit 11 has a receiving circuit 12, an exposure measuring circuit 13, a power supply 14 and a light source lamp 15. The output terminal of the exposure measuring circuit 13 is connected to a solenoid 16 with a shutter 17. The power supply 14 is connected to the receiving circuit 12 which is connected at the output terminals to the exposure measuring circuit 13. The power supply 14 connecting to the receiving circuit 12 is connected to the output terminals of a superposing circuit 19 provided within a camera 18. The superposing circuit 19 is connected at the input terminals to the output terminals of a transmitting circuit 20. A film wind motor 21 is connected through the superposing circuit 19 to the power supply 14. A beam splitter 23 is disposed facing an object lens 22 of the camera 18. A photosensor 24 is disposed on the side of the beam splitter 23. The output terminals of the photosensor 24 is connected to the transmitting circuit 20 which is further connected to a release switch 25. An endoscope 26 is provided with a light guide 27 and an image guide 28. The light guide faces at one end the light source lamp 15 with intervention of the shutter 17 therebetween. The image guide 28 faces at one end the object lens of the camera. The other ends of the light guide 27 and the image guide 28 face an object to be photographed.

Figure 2:
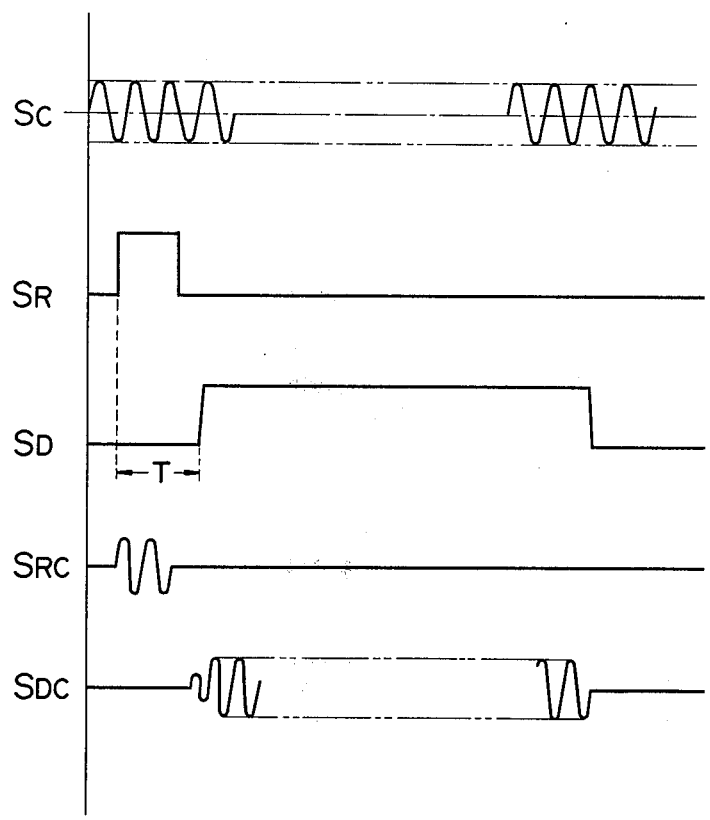
FIG. 2 is a set of waveforms useful in explaining the operation of the circuit shown in FIG. 1.

In the embodiment in FIG. 1, when the power supply 14 is turned on, the power supply lamp 15 lights up. Under this condition, when the release switch 25 of the camera 18 is closed, a release signal $S_R$ shown in FIG. 2 is produced. The time period that the release signal lasts is shorter than that taken for an operation that a mirror (not shown) provided within the camera rises and the film is exposed. In the transmitting circuit 20, a carrier wave $S_C$ shown in FIG. 2 is modulated by the release signal $S_R$ and the modulated signal $S_{RC}$ is transmitted from the transmitting circuit 20 to the superposing circuit 19. The superposing circuit 19 superposes the modulated signal $S_{RC}$ onto a motor drive line L connecting to the film wind motor 21 of the camera 18. The modulated signal $S_{RC}$ is transmitted to the receiving circuit 12, via the motor drive line L. In the receiving circuit 12, the modulated signal $S_{RC}$ is demodulated and the demodulated signal is transmitted to the exposure measuring circuit 13. The exposure measuring circuit 13 includes a solenoid drive means responsive to the demodulated signal corresponding to the release signal $S_R$ to drive the solenoid 16. As a result, the shutter sets up an optical path ranging from the light source lamp 15 to the light guide 27, thereby to allow light to go to the light guide 27. The light goes through the light guide 27 to irradiate the object 29. The reflecting light reflected at the object 29 enters the image guide 28. The reflecting light after passing through the image guide 28 passes through the objective 22 of the camera 18 and the beam splitter 23 to finally expose a film. Part of the reflecting light polarized by the beam splitter 23 enters the photosensor 24. Upon receipt of the polarized reflecting light, the photosensor 24 produces an electric signal (photocurrent signal) $S_D$ which in turn is supplied to the transmitting circuit 20 where it modulates the carrier wave $S_C$. As a result, the transmitting circuit 20 produces the modulated signal $S_{DC}$ which is then superposed onto the motor drive line L by the superposing circuit 19. The modulated signal $S_{DC}$ is demodulated in the receiving circuit 12 and then is applied to the exposure measuring circuit 13 where an exposure is measured. The exposure is measured by, for example, an integrator included in the exposure measuring circuit 13. When the exposure reaches a proper value, the exposure measuring circuit 13 provides a signal to deenergize the solenoid 16. In response to the signal, the shutter 17 restores to shut off the light incident upon the light guide 27. Then, the mirror within the camera falls to shut out the film, so that the shutter 17 is released again to allow the object to be observed. Every time that the mirror in the camera falls, the power source is connected to the wind motor thereby to wind the film by one frame. At the time that the winding of the film ends, the power source is disconnected from the film wind motor to stop it and be ready for the next photographing.

Figure 3:
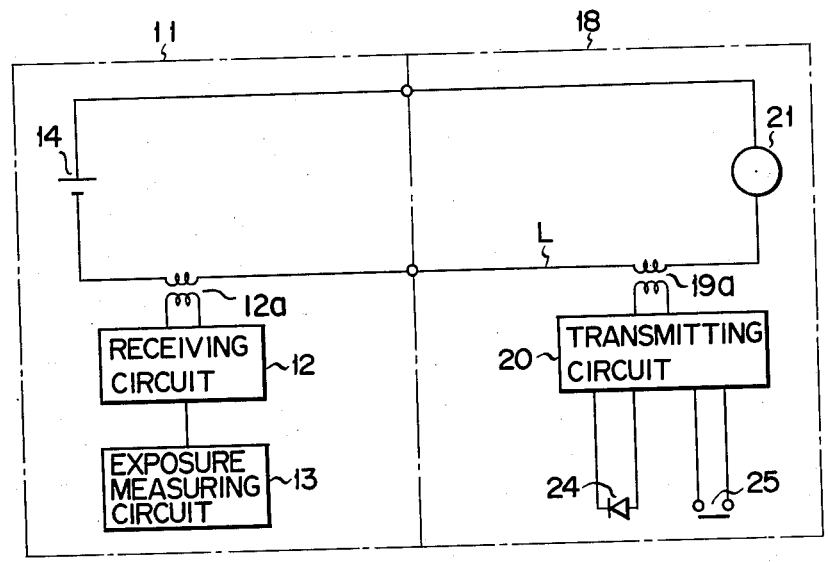
FIG. 3 is a circuit diagram of the combination of a light source unit and a camera.

FIG. 3 shows a circuit when a coupling transformer 19a is used for the superposing circuit 19. In the figure, a modulated signal from the transmitting circuit 20 is applied to the primary winding of the coupling transformer 19a and then is induced in the secondary winding connected to the motor drive line L. The modulated signal induced in the secondary winding of the coupling transformer 19a passes through the motor drive line L to enter the coupling transformer 12a of the light source unit 11 and then the receiving circuit 12 where it is demodulated.

Figure 4:
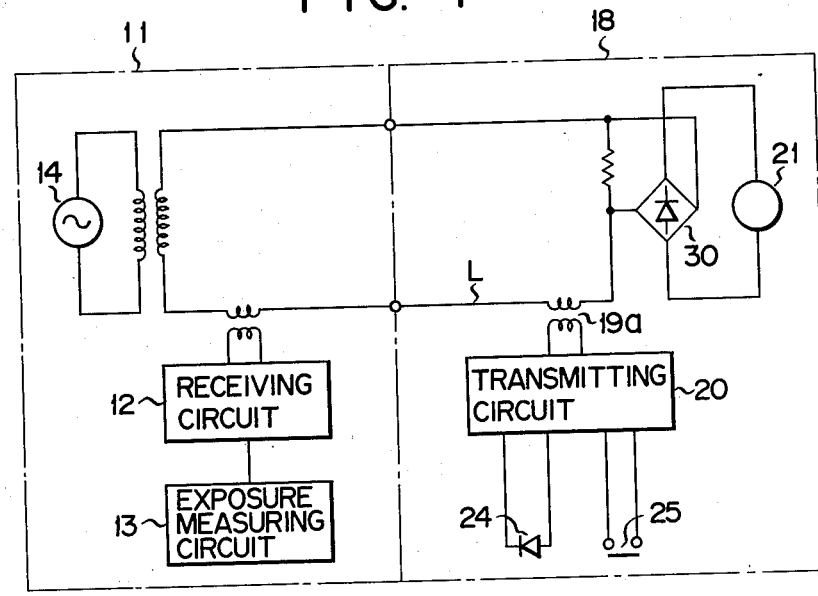
FIG. 4 shows a circuit diagram of the photographing apparatus which is another embodiment of the invention.

The embodiment shown in FIG. 4 uses an AC power source as the power source 14 of the light source unit 11. In this case, rectifier circuit 30 is provided in the motor circuit of the camera 18 and the motor 21 is driven by the rectified output signal. As in this case, when an alternate current, particularly an alternate current with a high frequency is used, it is possible to avoid an electric shock arising from current leaking into the camera and the endoscope.

Figure 5:
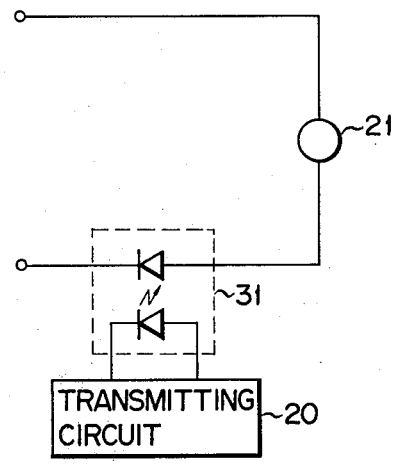
FIG. 5 is a circuit diagram of the camera in the photographing apparatus using a photocoupler as a superposing circuit, which is still another embodiment of the invention.

An embodiment of the invention shown in FIG. 5 employs a photocoupler for the superposing circuit.

Figure 6:
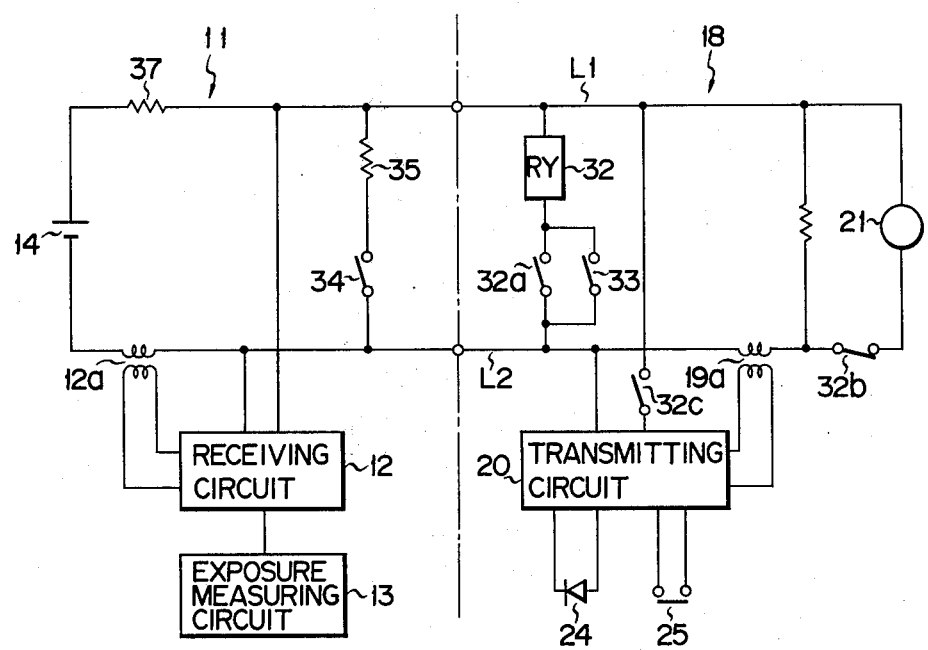
FIG. 6 is a circuit diagram of the photographing apparatus according to the invention in which a motor circuit is shut off at the time of photographing.

In an embodiment of the invention shown in FIG. 6, a relay 32 is coupled at one end with a line L1 and at the other end with a line L2 by way of a normally open contact 32a. To the normally open contact 32a is connected in parallel a film wind switch 33. To the motor 21 is connected in series the normally close contact 32b of the relay 32. The power source terminal of the transmitting circuit 20 is connected through a normally open contact 32c between the lines L1 and L2. In the light source unit 11, an exposure end contact 34 is connected through a resistor 35 between the lines L1 and L2.

In the embodiment shown in FIG. 6, at the time that the film is wound, a switch 33 has been closed and thus the relay 32 has been energized. In other words, the normally close contact 32b is open while the normally open contacts 32a and 32c are closed. Under this condition, when a release switch 25 is closed, an automatic exposure photographing is performed. After the photographing, the shutter 17 (FIG. 1) provided in the light source unit is closed. At this time, the contact 34 is also closed. Upon closing the contact 34, the voltage applied to the relay 32 falls to a value determined by the internal resistance of the power source 14 and the resistances of the resistors 35 and 37. The resistances of the resistors 35 and 37 are so selected that the voltage drop is lower than the holding voltage of the relay 32. As a result, the relay 32 is deenergized, the normally close contact 32b is closed and the normally open contacts 32a and 32c are open. Through this sequential operation electric power is supplied to the motor 21 and the motor 21 starts to rotate and to wind the film. On the other hand, power supply to the transmitting circuit 20 is stopped. After the relay 32 is deenergized, the contact 34 is released by its self-restoration. The switch 33 is released when the shutter 17 is closed. When the film is wound by a given amount by means of the film wind motor 21, the switch 33 is closed again to energize the relay 32. Accordingly, the photographing apparatus is ready for the next automatic exposure photographing. According to the embodiment, when the photographing apparatus enters the next automatic exposure photographing following the termination of winding the film, the power supply circuit to the film wind motor is shut off. Therefore, the automatic exposure accuracy is never deteriorated by noise of the motor at the time of photographing.

Figure 7:
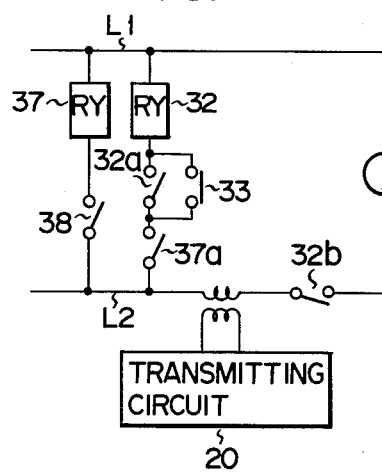
FIG. 7 is a circuit diagram of the photographing apparatus according to the invention with a timer, which is a modification of the embodiment shown in FIG. 6.

An embodiment shown in FIG. 7 employs a series circuit having a timer 37 and a mirror switch 38 provided between the lines L1 and L2. A timer switch 37a of the timer is connected in series to a parallel circuit having a relay normally open contact 32a and a switch 33. In the embodiment, when the mirror (not shown) returns to an observing position after the photographing termination, the mirror switch 38 closes to drive the timer 37 and to release the timer switch 37a. As a result, the relay 32 is deenergized to close the normally open contact 32b, so that the motor 21 starts to rotate. In other words, the winding of the film starts. After the period of time set by the timer 37, when the timer switch 37a is closed, the relay normally open contact 32a and the switch 33 have been open. Accordingly, the relay 32 is kept in deenergized state. After this, when the winding of the film terminates, the switch 33 is closed and the relay 32 operates again. As a result, the photographing apparatus is ready for the next photographing. The embodiment is so designed that, only the period of time set by the timer, rotation of the motor 21 is allowed. With this design, there is no influence of noise by the motor drive at the time of photographing.

Figure 8:
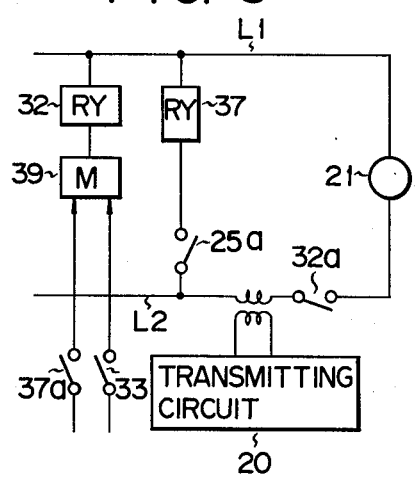
FIG. 8 is a circuit diagram of the camera of the photographing apparatus with a binary memory circuit, which is a further embodiment of the invention.

In an embodiment shown in FIG. 8, a series circuit composed of a timer 37 and a timer drive switch 25a is provided between the lines L1 and L2. The relay 32 is connected to a binary memory device 39. The binary memory device 39 is set in response to the closing of the timer switch 37a at the end of the timer operation while it is reset in response to the closing of the switch 33. In this embodiment, upon depression of the release button the timer drive switch 25a closes to drive the timer 37. The timer 37 is set to the maximum exposure time. Accordingly, when all the exposure operations are completed, the timer switch 37a closes. Upon this, the binary memory circuit 39 is set while at the same time the relay 32 is energized. As a result, the relay normally open contact 32a is closed to device the motor. When the motor winds the film by a given amount, the switch 33 closes to reset the binary memory circuit 38. Accordingly, the relay 32 is deenergized to release the relay contact 32a and to stop the motor 21. In this embodiment, the automatic exposure photographing is performed within the time period set by the timer 37. Therefore, there is eliminated an influence of noise by the motor.

As described above, the release signal and the exposure information signal are superposed onto the motor drive line used for feeding electric power to the film wind motor. Accordingly, there is no need for another signal line for transmitting those signals. No provision of the another signal line reduces the number of terminals to electrically connecting the light source unit, the endoscope and the signal lines. The result is that the occurrence of poor contact is minimized and the construction of the connection terminals is simplified. Moreover, since the film wind motor is stopped under the automatic exposure photographing, there is no fear that the accuracy of the automatic exposure photographing is degraded.

What is claimed is:

1. A photographing apparatus for an endoscope for making an automatic exposure photograph through the combination of a light source unit, an endoscope and a camera for endoscope photograph, wherein the camera for endoscope photograph includes a photosensing element for producing a photocurrent signal, a transmitting circuit for transmitting a release signal produced in response to the operation of a release switch and a modulated signal modulated by the photocurrent signal derived from said photosensing element, and a superposing circuit for superposing the modulated signal onto a motor drive line connected to a film wind motor, and the light source unit includes a demodulating circuit for demodulating the modulated signal transmitted from said transmitting circuit and an exposure measuring circuit for measuring an optimum exposure by using a demodulated signal from said demodulating circuit.

2. A photographing apparatus according to claim 1, wherein said camera is comprised of a timer connected to said motor drive line, a timer drive means connected to said timer which operates in synchronism with said release switch to drive said timer, and a binary memory circuit which is set by an operation end signal from said timer and is reset by a film wind termination signal.

3. A photographing apparatus according to claim 1, wherein said light source unit has an AC power source, said camera has a rectifying circuit connected to said AC power source of said light source unit, and said film wind motor is driven by a DC power obtained through the rectification by said rectifying circuit.

4. A photographing apparatus according to claim 1, wherein said transmitting circuit operates in response to a switch which operates complementarily with respect to a relay contact connected in series to said motor.

5. A photographing apparatus according to claim 1, wherein said superposing circuit is a transformer coupling means for coupling electromagnetically said transmitting circuit and said motor drive line.

6. A photographing apparatus according to claim 1, wherein said superposing circuit is a photocoupling means for coupling optically said transmitting circuit and said motor drive line.

7. A photographing apparatus according to claim 1, wherein said camera includes a film wind termination switch which closes at the termination of the winding of a film, and voltage dropping means having a normally open contact connected in parallel to said film wind termination switch, a normally closed contact connected in series to said motor, and a drive relay connected in series to a parallel switch circuit composed of said switch and said normally closed contact, whereby a voltage applied to said motor at the termination of the winding of film is controlled to be smaller than a holding voltage of said drive relay.

* * * * *